US012648805B2

(12) United States Patent　　　　　　(10) Patent No.:　US 12,648,805 B2
Newton　　　　　　　　　　　　　　　(45) Date of Patent:　Jun. 9, 2026

(54) DEVICE AND METHOD FOR DETECTING FAULTS IN A SHIELDED INSTRUMENT

(71) Applicant: Encision Inc., Boulder, CO (US)

(72) Inventor: David Newton, Longmont, CO (US)

(73) Assignee: Encision, Inc., Boulder, CO (US)

( * ) Notice:　Subject to any disclaimer, the term of this patent is extended or adjusted under 35 U.S.C. 154(b) by 234 days.

(21) Appl. No.: 18/663,907

(22) Filed:　May 14, 2024

(65)　　　　　Prior Publication Data

US 2025/0009409 A1　　Jan. 9, 2025

Related U.S. Application Data

(63) Continuation of application No. 17/685,156, filed on Mar. 2, 2022, now Pat. No. 11,998,259, which is a continuation of application No. 15/937,086, filed on Mar. 27, 2018, now Pat. No. 11,291,494, and a continuation of application No. 14/302,281, filed on Jun. 11, 2014, now Pat. No. 9,956,027.

(51) Int. Cl.
*A61B 18/12*　　　(2006.01)
*A61B 18/00*　　　(2006.01)
(52) U.S. Cl.
CPC　*A61B 18/1233* (2013.01); *A61B 2018/00678* (2013.01); *A61B 2018/00708* (2013.01); *A61B 2018/00827* (2013.01); *A61B 2018/1226* (2013.01)

(58) Field of Classification Search
CPC . A61B 18/1206; A61B 18/1233; A61B 18/16; A61B 2018/00767; A61B 2018/00827; A61B 2018/00898; A61B 2018/0089
See application file for complete search history.

(56)　　　　　References Cited

U.S. PATENT DOCUMENTS

| | | | |
|---|---|---|---|
| 5,312,401 A * | 5/1994 | Newton | A61B 18/14 |
| | | | 606/42 |
| 5,818,237 A * | 10/1998 | Zuercher | H02H 1/0015 |
| | | | 361/93.6 |
| 2009/0112204 A1 * | 4/2009 | Aronow | A61B 18/1233 |
| | | | 606/34 |

* cited by examiner

*Primary Examiner* — Eun Hwa Kim
(74) *Attorney, Agent, or Firm* — NOD Law PC

(57)　　　　　ABSTRACT

A device and method for detecting faults in a shield of an electrosurgical instrument is described. The device has a relay configured to selectively interrupt power to the electrosurgical instrument, monitoring circuitry configured to monitor a shield in the electrosurgical instrument, control circuitry to control the relay, and a battery power source. The monitoring circuitry has an envelope detector and a detected average shield current detector. The monitoring circuitry is configured to compare a shield current peak value to a shield current peak threshold value, and to compare a detected average shield current value to a detected average shield current threshold value. The device is further configured to operatively couple an active electrode of an electrosurgical instrument and a return electrode to an electrosurgical generator.

20 Claims, 12 Drawing Sheets

DEVICE AND METHOD FOR DETECTING FAULTS IN A SHIELDED INSTRUMENT

CLAIM OF PRIORITY UNDER 35 U.S.C. § 119

The present application for Patent is a continuation of U.S. patent application Ser. No. 17/685,156, entitled "DEVICE AND METHOD FOR DETECTING FAULTS IN A SHIELDED INSTRUMENT" filed Mar. 2, 2022, which is a Continuation of Ser. No. 15/937,086, entitled "DEVICE AND METHOD FOR DETECTING FAULTS IN A SHIELDED INSTRUMENT" filed Mar. 27, 2018, which is a Continuation of patent application Ser. No. 14/302,281, now U.S. Pat. No. 9,956,027, entitled "DEVICE AND METHOD FOR DETECTING FAULTS IN A SHIELDED INSTRUMENT" filed Jun. 11, 2014, which is expressly incorporated by reference herein as if presented in its entirety.

COPYRIGHT

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all rights available under copyright law.

FIELD OF THE INVENTION

Aspects of the present invention relate to devices and methods for detecting faults in electrosurgical instruments powered by electrosurgical generators. In particular, but not by way of limitation, the present invention relates to systems and methods for detecting faults in the insulation of a shielded electrosurgical instrument.

BACKGROUND OF THE INVENTION

Laparoscopic or electrosurgical instruments may have an insulated, conductive safety shield around an active electrode of the electrosurgical instrument. During surgery, the physician can monitor current passing through the shield to prevent the shield from causing unintended burns to the patient.

Various manners of monitoring the shield current are disclosed in U.S. Pat. No. 5,312,401 to Newton et al., U.S. Pat. No. 5,688,269 to Newton et al., U.S. Pat. No. 8,007,494 to Taylor et al., and U.S. Pat. No. 8,460,284 to Aronow, the disclosures of which are incorporated herein by reference in their entirety.

It should also be noted that, historically, the typical surgical equipment, including power supplies, signal processing, computer, and output devices are connected to a mains or line ground which is the same as the ground for the input power. Signals which come from points that are not referenced to mains ground must be isolated using floating power supplies and perhaps optical elements or transformers for the signals themselves. Further details of this construction are explained in U.S. Pat. No. 5,312,401 to Newton et al.

Although present devices are functional, their set-up and use require significant oversight by operating room personnel, and they are bulky and difficult to transport throughout the hospital. Accordingly, a system and method are needed to address the shortfalls of present technology and to provide other new and innovative features.

SUMMARY OF THE INVENTION

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

The present invention can provide a system and method for detecting faults in the insulation of a shielded instrument. In one exemplary embodiment, the present invention can include a device for detecting insulation faults in a shielded electrosurgical instrument. The device includes a relay configured to selectively interrupt power to the electrosurgical instrument, monitoring circuitry configured to monitor electrical signals associated with a shield in the electrosurgical instrument, and circuitry, responsive to the monitoring circuitry, configured to control the relay. The device also includes a battery power source. The monitoring circuitry further comprises an envelope detector and a wideband averaging detector and is configured to compare a shield current peak value to a shield current peak threshold value. The monitoring circuitry is also configured to compare a detected average shield current value to a detected average shield current threshold value. The device is also configured to operatively couple an active electrode of an electrosurgical instrument and a return electrode to an electrosurgical generator.

A method for detecting faults within a shield of an electrosurgical instrument is also disclosed. The method comprises connecting a device for detecting insulation faults within a shield of an electrosurgical instrument, the device powered by an independent battery power source. The device is connected to an electrosurgical generator, the electrosurgical generator configured to deliver power to an electrosurgical instrument. The method also comprises monitoring set up signals of the electrosurgical instrument, the set-up signals including a connect sense and a battery power sense; monitoring electrical signals associated with a detected average shield current and a shield current peak; comparing the electrical signals with threshold electrical signals; and controlling alarm indicators.

As previously stated, the above-described embodiments and implementations are for illustration purposes only. Numerous other embodiments, implementations, and details of the invention are easily recognized by those of skill in the art from the following descriptions and claims.

BRIEF DESCRIPTION OF THE DRAWINGS

A more complete understanding of the present invention is apparent and more readily appreciated by reference to the following Detailed Description and to the appended claims, when taken in conjunction with the accompanying Drawings, wherein:

DETAILED DESCRIPTION

Figure 1:
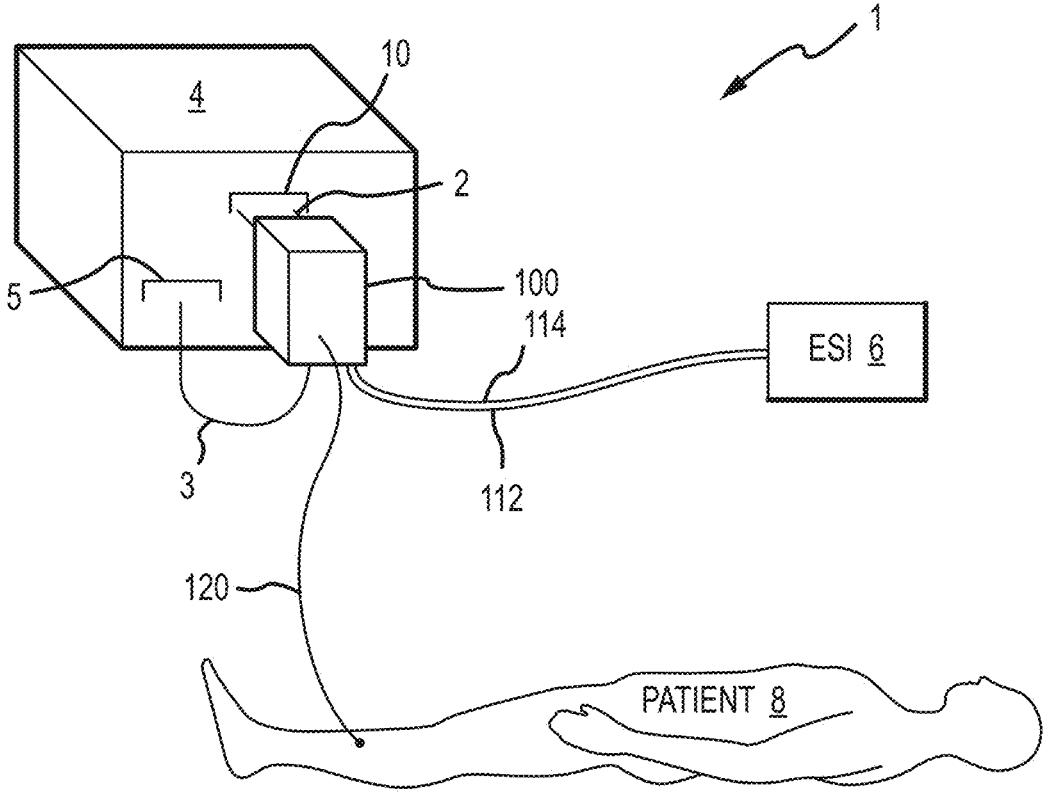
FIG. 1 is an exemplary isometric view of a surgical environment.

Referring now to the drawings, where like or similar elements are designated with identical reference numerals throughout the several views, and referring in particular to FIG. 1, shown is an exemplary surgical environment 1. For the purpose of this disclosure, it should be understood that the word "exemplary" is used herein to mean "serving as an example, instance, or illustration." Any embodiment described herein as "exemplary" is not necessarily to be construed as preferred or advantageous over other embodiments. The surgical environment 1 includes a monitoring device 100, an electrosurgical generator 4, an electrosurgical instrument 6, and a patient 8.

The device 100 is configured to be electrically coupled to the electrosurgical instrument 6, the electrosurgical generator 4, and the patient 8, to detect faults in the electrosurgical instrument 6. The device 100 is operatively coupled to the electrosurgical instrument 6 via an active electrode cable 112 and a shield current return cable 114, which may include two wires, one of which may be connected to circuit ground. The active electrode cable 112 and the shield current return cable 114 may be enclosed by a common sheath (not shown) to simplify cable management.

The device 100 is further configured to couple the active electrode cable 112 to the electrosurgical generator 4 via an active cable link 3, which may be a short cable, as shown, or any other connecting mechanism suitable for the high currents and voltages expected, including a manual switching mechanism or integral pin and socket mechanism that would allow a simultaneous connection. More specifically, active cable link 3 provides a means for operatively coupling the device 100 to any one of a variety of electrosurgical generators 4, which may not be standardized across the industry. Active cable link 3 may also require a second coupling step from the user, thus minimizing risk of unintended coupling.

Similarly, the device 100 operatively couples a return electrode cable 120 to the electrosurgical generator 4 via return electrode connector 2 coupled to a return electrode connector 10. In this embodiment, within the device 100, the shield current return cable 114 is operatively coupled to the generator interface connector. It should be understood that, although shown as a generator interface connector and return electrode connector 10, the device 100 may operatively couple the return electrode cable 120 to the electrosurgical generator 4 in any manner suitable to the expected working conditions. Further, one or more of the active cable link 3, the return electrode cable 120, the active electrode cable 112, and the shield current return cable 114 may be permanently pre-attached to the device 100. The return electrode connector 2 and active cable link 3 may comprise male plugs, and the return electrode connector 10 and active connector 5 may comprise female receptacles. However, it should be understood that any electrical coupling system may be employed, including, but not limited to, male plugs, female plugs, male jacks, female jacks or any other suitable mating system.

Figure 2:
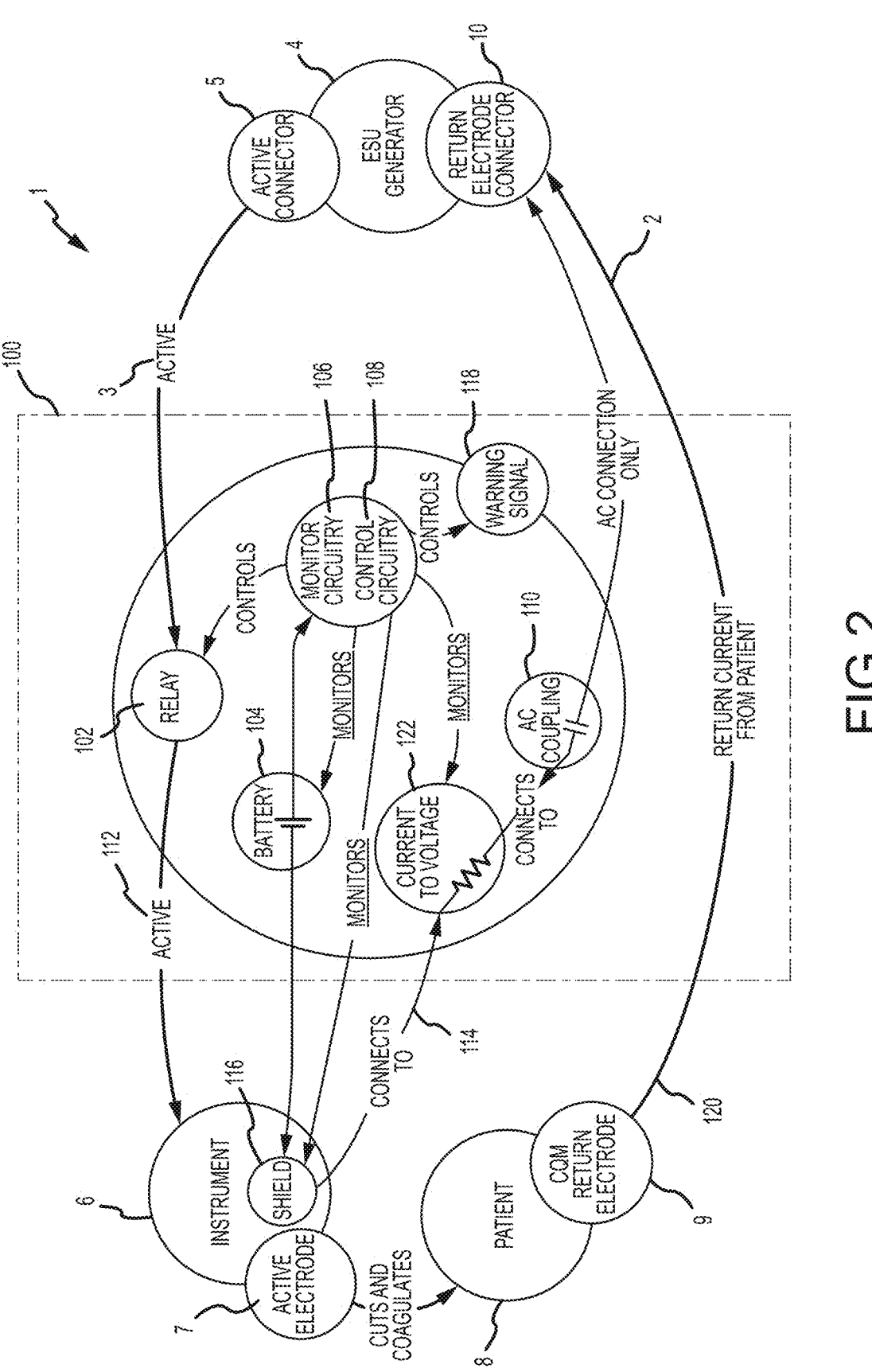
FIG. 2 is a functional context diagram of an embodiment of the present invention.

Turning now to FIG. 2, illustrated is an exemplary operational context diagram of the system 1 discussed above. At a high level, the device 100 is configured to electrically couple an electrosurgical generator 4 to an electrosurgical instrument 6 by way of an active electrode cable 112, and a return electrode cable 120 to an electrosurgical generator. The device 100 is configured to establish a closed circuit between the electrosurgical generator 4, the electrosurgical instrument 6, and the patient 8, as well as to provide a circuit ground, and a shield current return mechanism. A contact quality monitored (CQM) return electrode 9 may couple the return electrode cable 120 to the patient 8.

As discussed above, the active electrode cable 112 is configured to deliver a desired power to the electrosurgical instrument 6, while the return electrode cable 120 is configured to complete the circuit for surgery. However, when faults are detected, it is necessary to interrupt power to the electrosurgical instrument 6, within about 0.6 seconds or less, to prevent thermal burns or overheating of tissue, and such interruption is achieved by way of a relay 102, as shown. The relay 102 may be any relay 102 suitable for passing the high currents and voltages expected in the course of laparoscopic surgery or other surgical interventions. In some embodiments, the relay may be a vacuum reed design with a package that provides adequate clearance between the coil and contact, as well as sufficient internal insulation to withstand 5000 V peak voltage. Provision for this clearance is present in the relay connections and in other areas and this permits a peak voltage rating for the product of 4100 V including required safety margins. It should be understood that the required safety margins, although generally around 20% in the industry, may change, thus necessitating a change in the clearance.

During operation, normal currents flow through the shield 116 and through the device 100 to the return electrode cable 120 even when no fault exists. This is due to the high electrosurgical voltages applied to the active electrode 7, as well as the inherent capacitance of the electrosurgical instrument 6 and active electrode cable 112. Fault currents flow through the same path. However, fault currents are distinguished from normal currents by two recognizable characteristics of the faults. First, the fault currents tend to be larger than normal currents. The fault currents also tend to have a higher current peak value, due to inconsistent conduction through defects in the insulation of the shield 116. It is critical to detect fault currents quickly and reliably to prevent overheating of patient tissue.

As seen in FIG. 2, monitoring circuitry 106 is in electrical communication with control circuitry 108 and the instrument shield, and is configured to monitor electrical signals from the instrument shield 116, which may include detectable physical quantities or impulses (such as voltage, current, or magnetic field strength, by which messages or information can be transmitted. The control circuitry 108 is responsive to signals from the monitoring circuitry 106 and is configured to initiate a desired response in various hardware or active components of the device 100. That is, the control circuitry 108, upon receipt of a fault signal from the monitoring circuitry 106, may open or close the relay 102 as necessary. In some embodiments, the control circuitry 108 may cause audible, visual, or other warning signals 118 to be activated in response to a signal from the monitoring circuitry 106 that a fault condition exists.

As further seen in FIG. 2, the monitoring circuitry 106 and the control circuitry 108 may be integrated in a single unit; however, it should be understood that the monitoring circuitry 106 and the control circuitry 108 may be separate and distinct units, or partially distinct units, as will become apparent in the discussion below.

Figure 3:
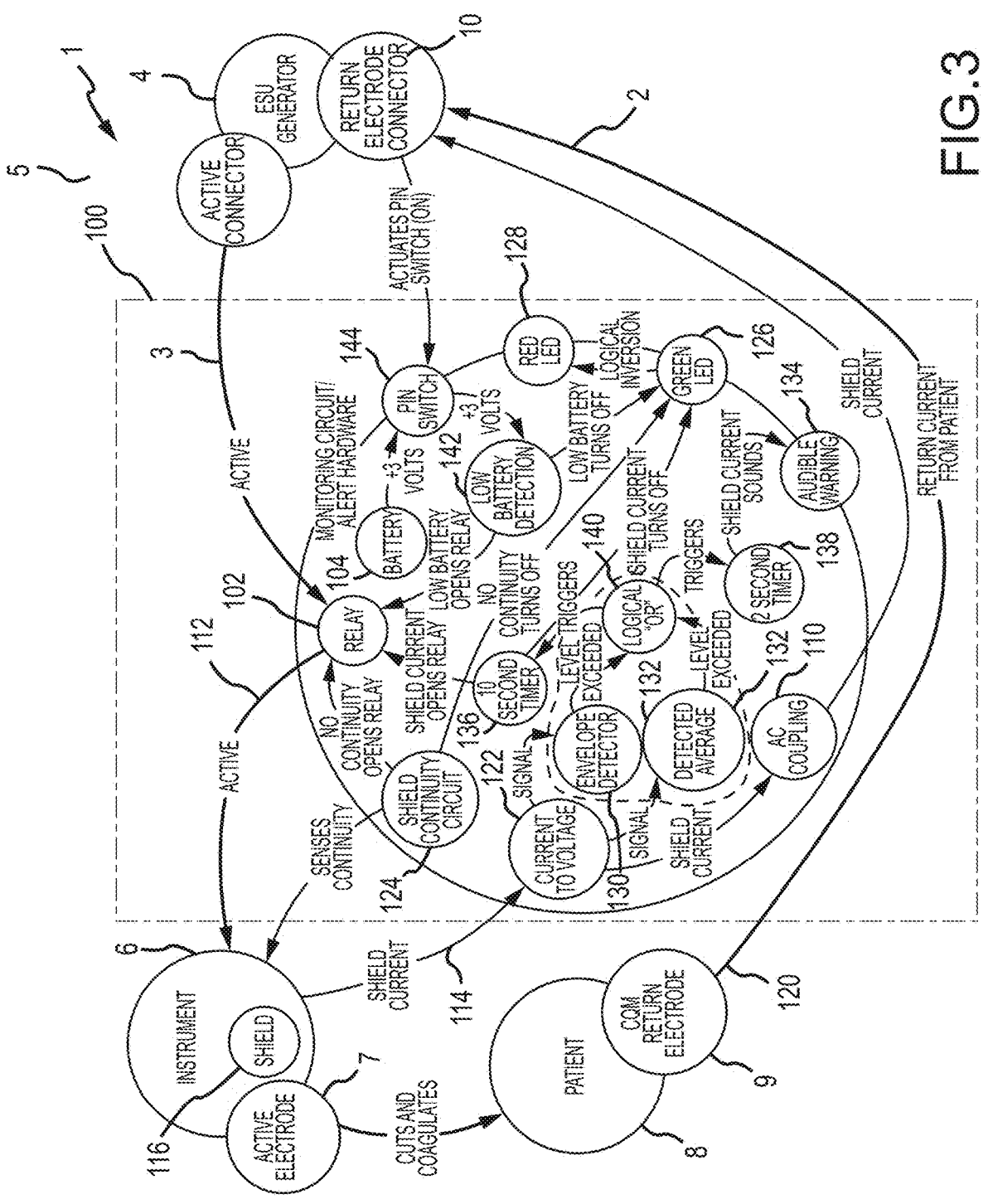
FIG. 3 is a detailed functional context diagram of an embodiment of the present invention.

Turning now to FIG. 3, illustrated is a detailed operational context diagram of one embodiment of the system 1 described above. As seen, the device 100 may include a shield continuity circuit 124. The shield continuity circuit 124 is configured to test electrical continuity across the shield 116. If the shield 116 is malfunctioning, the shield continuity circuit 124 is configured to open the relay 102, as well as to turn off a green LED 126. A logical inversion operation serves to turn a red LED 128 on. As should be apparent throughout this disclosure, the monitoring circuitry 106 and control circuitry 108 may comprise portions of the shield continuity circuit 124, the green LED 126 and the red LED 128 components.

Returning to FIG. 3, the device 100 may include as outputs one or more green LEDs 126 and red LEDs 128, and a relay 102 that may interrupt power delivered to the electrosurgical instrument 6. The relay 102 is closed when the green LED 126 is illuminated during ready conditions— that is, the monitoring circuitry 106 does not detect a fault from the low battery detector 142, the envelope detector 130 or the shield current average detector 132, which will be discussed further below. Similarly, the relay 102 is open when the red LED 128 or other warning signal 118 is activated under fault conditions.

As discussed above, a current to voltage converter 122 may be provided for converting a return shield current to a voltage signal. This voltage signal is monitored by the envelope detector 130, which is configured to detect peak or peak-to-peak values, and a shield current average detector 132, which may be a wideband averaging detector, such as, but not limited to, a full wave rectified average (FWRA), a half wave rectified average, a mean squared, a root mean squared, or a mean power detector.

The envelope detector 130 is configured to compare the current peak to a preset threshold current peak value. If the current peak is greater than the preset threshold value, the relay 102 may be temporarily opened to interrupt power to the instrument 6. Simultaneously, an audible warning 134 may be activated. The interruption of power and the activation of the audible warning 134 may both be set to a limited timeframe. For example, the envelope detector 130 may include a 10 second timer 136 to limit the interruption of power to the device to 10 seconds, and a 2 second timer 138 may be included to limit the audible warning 134 to a 2 second warning. The 10 second interruption is particularly effective in allowing the affected components of the electrosurgical instrument 6 to cool to a safe level when the device 100 quickly detects a fault and interrupts power. Here, the device 100 may be configured to reliably detect a fault and interrupt power to the electrosurgical instrument 6 within about 10-130 milliseconds, before significant tissue damage occurs, which is significantly faster than the 0.6 second time needed for the instrument to heat to a temperature sufficient to cause tissue damage, or about 44 degrees Celsius. Likewise, a 2 second timer 138 may be sufficient to alert a surgical team of a fault without introducing unnecessary added distractions to the surgical team. It should be understood, however, that other timings may be desired or chosen. In some situations, perhaps no or a longer, or shorter, or repeated audible warning is desired.

Continuing with FIG. 3, the device 100 also includes a shield current average detector 132, which, in some embodiments, may be a wideband averaging detector as previously discussed. The shield current average detector 132 is configured to compare the shield current detected average to a preset threshold value. If the shield current detected average is greater than the preset threshold value, the relay 102 may be temporarily opened to interrupt power to the electrosurgical instrument 6, and an audible warning 134 may be activated, as discussed above. It should be understood that, although a FWRA method is exemplified in FIG. 3, any averaging technique, such as a wideband average, may be used.

Also, as discussed above, a current to voltage converter 122 may be provided for converting the shield current to a voltage signal. This voltage signal is monitored by the envelope detector 130 and the shield current average detector 132. These circuits develop voltages which are compared with thresholds to derive fault signals.

The device 100 may include monitoring circuitry 106 comprising an OR function 140. That is, if either the peak shield current or the shield current detected average exceeds a threshold value, power to the electrosurgical instrument 6 may be interrupted. In some embodiments, the peak shield current or the shield current detected average must exceed a threshold value for a predetermined period of time for a fault situation to be indicated, so as to distinguish fault situations from electrical noise. In some embodiments, the device 100 may include monitoring circuitry comprising a SUM function, wherein the sum of the peak shield current and the shield current detected average must exceed a threshold value before a fault situation is indicated. In some embodiments, the sum must exceed a threshold value for a predetermined length of time for a fault situation to be indicated. In some embodiments, the device 100 may include monitoring circuitry comprising a PROPORTIONAL function, wherein the ratio between the peak shield current and the shield current detected average must deviate from a threshold value before a fault situation is indicated. In some embodiments, the ratio between the peak shield current and the shield current detected average must deviate from a threshold value for a predetermined length of time for a fault situation to be indicated. In some instances, the OR function, the SUM function, or the "PROPORTION" function may be configured to determine an approach to a second threshold value, the second threshold value being indicative of a potential, though not developed, fault.

The device 100 is powered by an independent battery power source 104 and does not require power from the electrosurgical generator 4, and a pin switch 144 may be included in the device 100 to switch the battery power source 104 to "on" when the device 100 is coupled to the return electrode connector 10. The battery power source 104 is referenced to circuit ground via the shield conductor. To detect proper functioning of the battery power source 104, a low battery detector 142 is provided. If the low battery detector 142 senses that the battery power source 104 is below a threshold charge, the green LED 126 is turned off, and the red LED 128 is activated.

In some embodiments, the device 100 is powered by a CR02 Lithium Manganese cell, although any battery power source 104 suitable for providing a nominal output, perhaps in the range of 2.9 volts, adequate to allow direct activation of the circuitry (including monitoring circuitry 106 and control circuitry 108), LEDs 126, 128, audible warning 134 and relay 102 is contemplated.

Figure 3A:
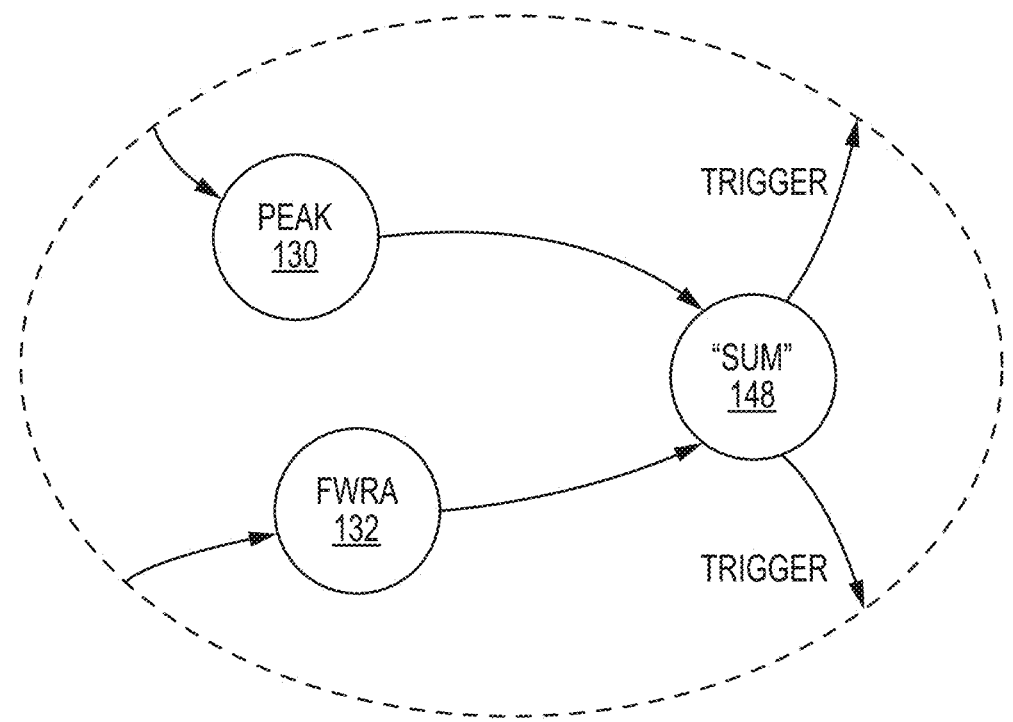
FIGS. 3A-3C are alternative functional context diagrams of the embodiment illustrated in FIG. 3.
Figure 3B:
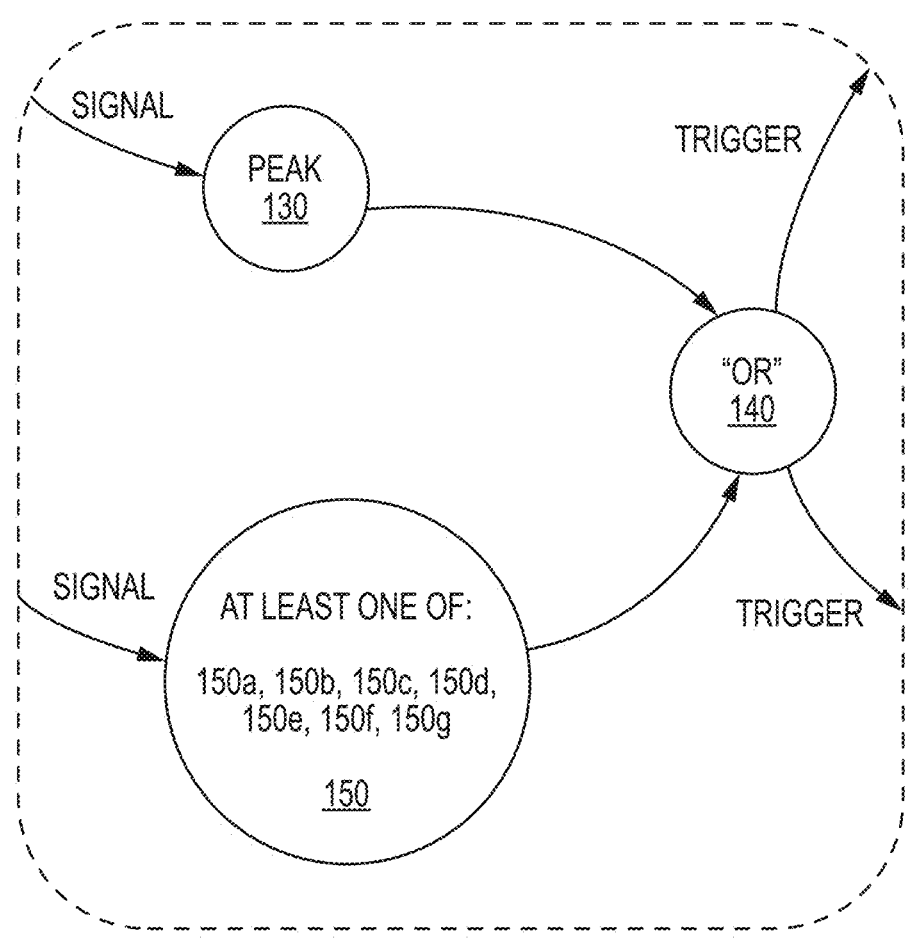
Figure 3C:
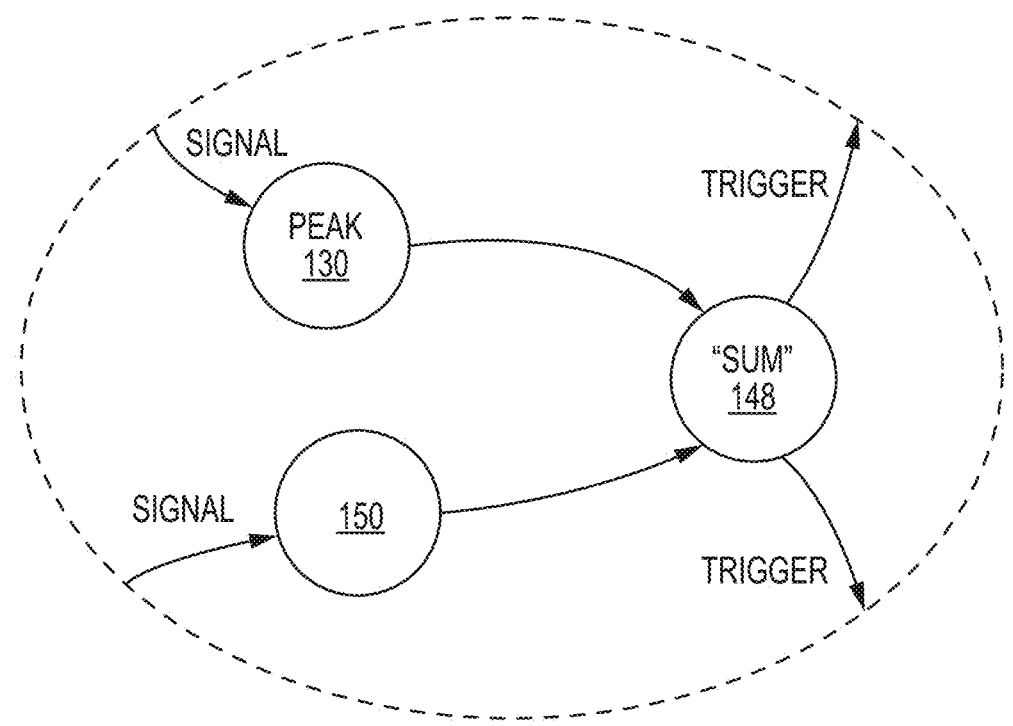

Turning now to FIGS. 3A-3C, alternate embodiments are now discussed. For example, in FIG. 3A, it is shown that, instead of an OR function, the device 100 may include a SUM function 148. That is, a fault is detected where the sum of the peak value and the current detected average, which may be a wideband average, such as an FWRA calculation, exceeds a threshold value. The device 100 may be configured to require the sum to exceed a threshold value for a predetermined length of time before detecting a fault.

In FIG. 3B, it is shown that, instead of an FWRA, the device may include a different RF parameter detector 150 with an OR function 140. That is, a fault is detected where the peak value or the RF parameter exceeds a threshold value. The threshold value of the peak value and the threshold value of the RF parameter are not necessarily the same. The device 100 may be configured to require the peak value or the RF parameter to exceed a threshold value for a predetermined length of time before detecting a fault. The RF parameter detector 150 may be configured to detect one or more of: the detected average, real power in the shield 150a, the root mean square (RMS) of the real part of the shield current 150b, the RMS of the total current in the shield 150c, the RMS of the total current in the shield below a certain active electrode voltage (referenced to the return electrode) 150d, the magnitude of the impedance or capacitance between the active electrode and the shield 150e, the resistance between the active electrode and the shield 150f, and the active electrode voltage (referenced to the return electrode) in combination with other signals 150g. Some methods for detecting the RF signals are described in U.S. Pat. No. 8,460,284.

In FIG. 3C, it is shown that a SUM function 148 may be used in combination with an envelope detector 130 and an RF parameter detector 150 much like those discussed in relation to the embodiment shown in FIG. 3B. As previously mentioned, a PROPORTIONAL function may be used instead of the SUM or OR functions.

Figure 4:
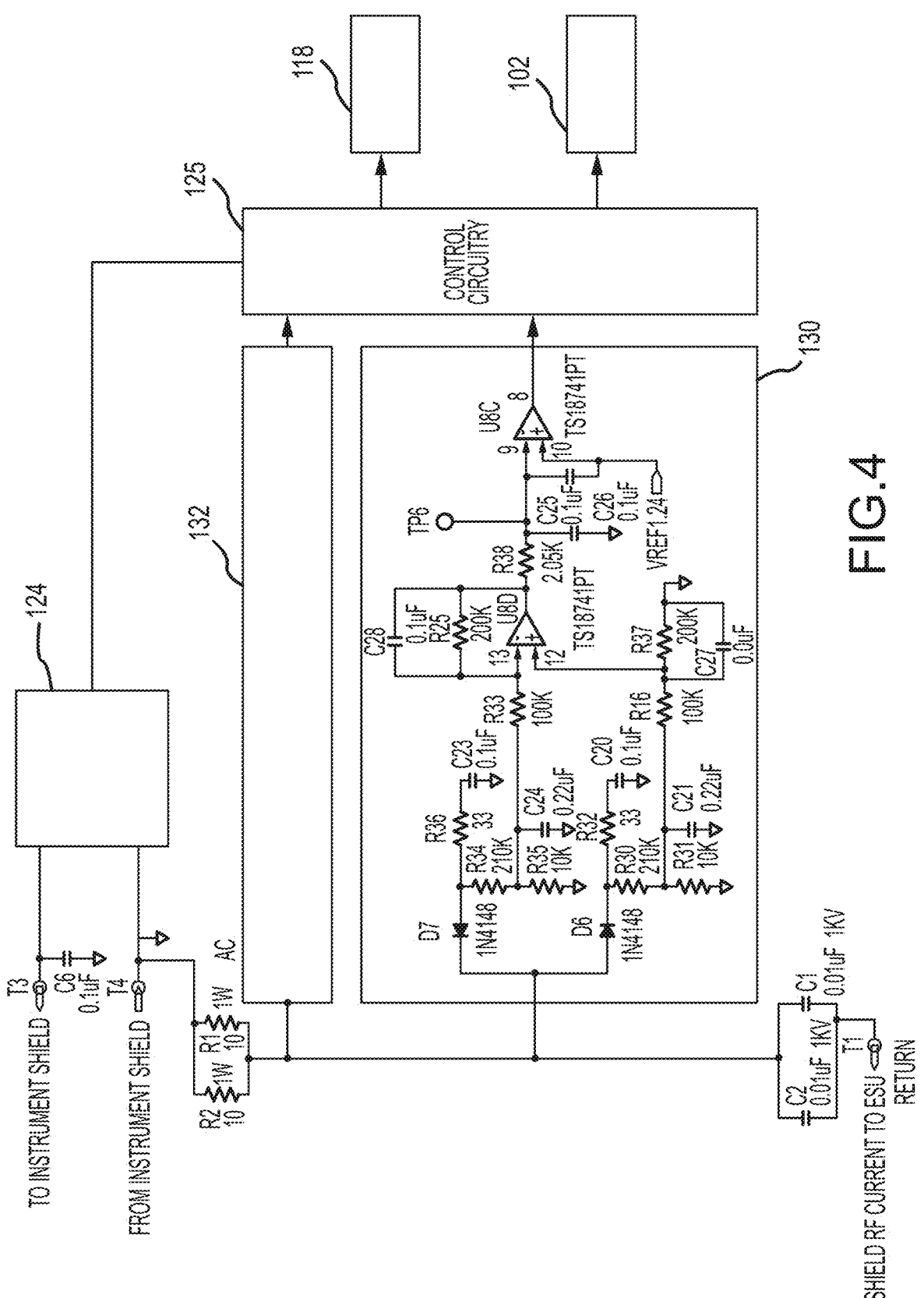
FIG. 4 is a mixed circuit-block diagram of an embodiment the present invention.
Figure 4A:
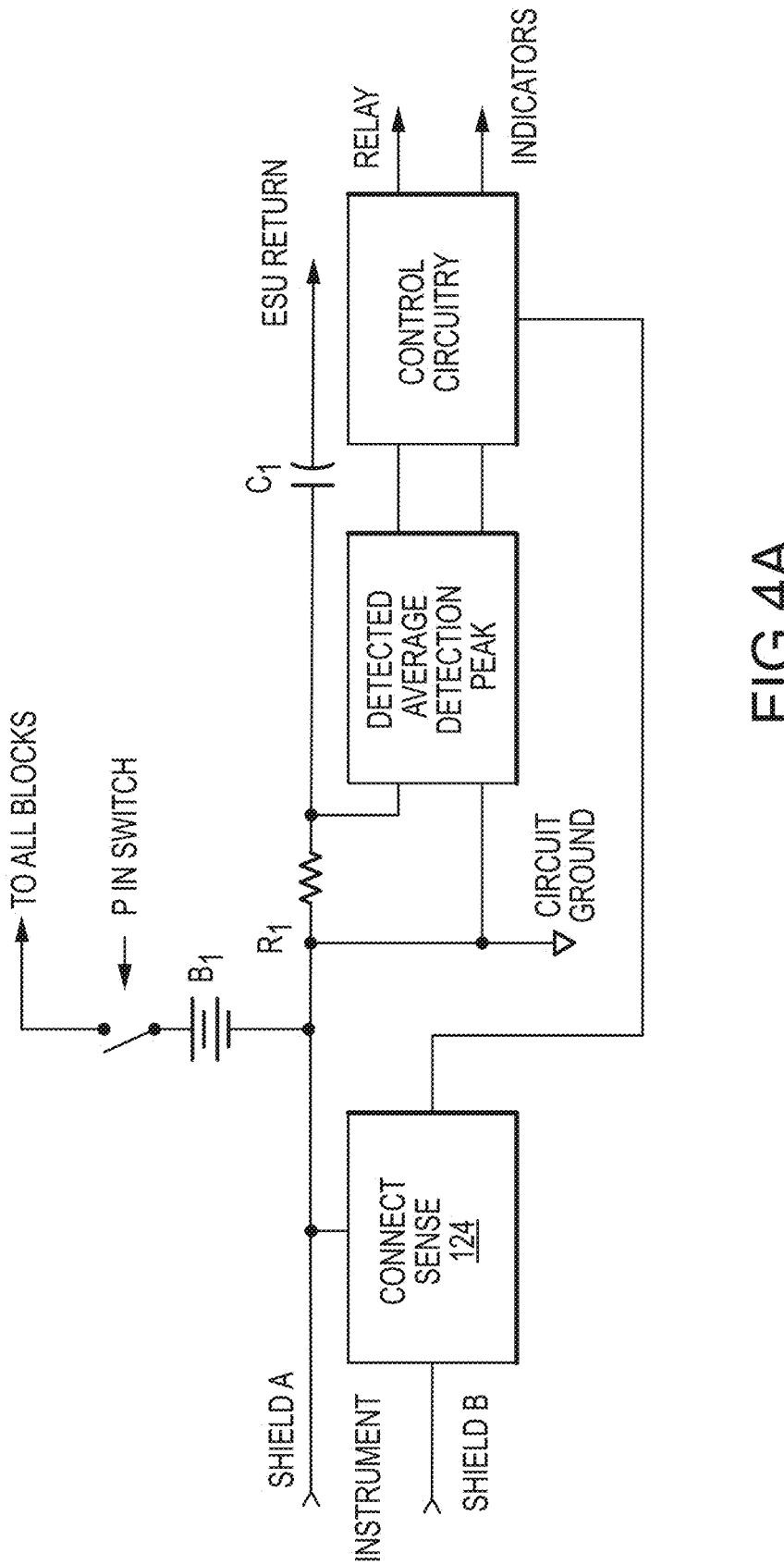
FIG. 4A is a detailed mixed circuit-block diagram of the embodiment illustrated in FIG. 4.

Turning now to FIGS. 4 and 4A, combined circuit and block diagrams of embodiments of a portion of the monitoring circuitry 106 and control circuitry 108 are now discussed. As seen, the shield connection is sensed at block 124, which may be a sensor in the monitoring circuitry 106 previously described. In FIG. 4A, the shield current is sensed at R1, while C1 provides a low frequency isolation function and B1 is the battery power source. The battery voltage is sensed and monitored, as well as current passing through the insulation. The sensed variables are logically monitored and combined to determine the ready (green LED) and fault (red LED) conditions. It should also be noted that the connect sense 124 and the control circuitry are both connected to the same circuit ground, which reduces the overall size and electrical isolation elements required in the device 100.

Continuing with FIG. 4A, to indicate whether an instrument shield is connected, a shield continuity circuit 124 includes a pair of shield A and shield B wires, which are, in turn, coupled to the shield of an electrosurgical instrument. If no insulation fault is detected, the shield is properly connected, and the battery is sufficiently charged, control circuitry, which may be a part of monitoring circuitry 106 and/or control circuitry 108, is configured to allow the relay 102 to remain closed, and for the warning 118 to indicate ready conditions. If an insulation fault is detected, and the shield is not properly connected, or the battery is not sufficiently charged, the control circuitry is configured to open relay 102, and to cause the warning 118 to indicate a fault or not-ready condition. Configuring the device 100, and hence the system 1, as shown in FIGS. 4 and 4A, that is, by connecting the circuit ground to the shield, near the return electrode potential, eliminates the necessity of large and expensive components to isolate the power supply and the fault current signal paths.

Continuing with FIG. 4A and FIG. 2, it should be noted that the grounding scheme shown includes a grounding point that is common for all the circuitry. The connect sense circuitry, current sensing resistor, detection circuitry, battery and control components are all connected to a common circuit ground point. This is close to the return electrode potential but not exactly the same due to current flowing through the current sense resistor R1 and the AC Coupling capacitor C1.

Sensing of an insulation fault condition is via processing of signals provided by a current sensing resistor and connected to rectification, filter, amplifier, and comparator circuits. That is, both a shield current average detector 132 and an envelope detector 130 are employed, with the envelope detector 130 comprising circuitry, or equivalents, thereof, as shown in FIG. 4.

As is further seen in FIG. 4, R1 and R2 are configured to develop a voltage proportional to the current sensed. The voltage is directed to two channels of current processing: the shield current average detector 132, which may be a full-wave rectified average (FWRA) and the envelope detector 130. C1, C2 connect the path to the shield current return and provide a block for Faradic current that may develop, which would otherwise cause muscle stimulation in the patient under fault conditions.

D1, D2, C3 and C4 provide voltages that are proportional to the positive and negative current averages. U8A sums these to output a voltage proportional to the shield current detected average value for the high frequency current waveform. This is compared to a fixed threshold value and if above the threshold, triggers an alert.

Continuing with FIG. 4, it is shown that D6, D7, C20 and C23, with additional filtering, provide voltages that are proportional to the positive and negative current peaks. These are summed by U8D so that the output voltage is proportional to the shield current peak to peak value. This is compared to a fixed reference, and if the value is greater than the threshold value, the control is configured to trigger an alert and interruption of power. For both current channels from the shield current average detector 132 and the envelope detector 130, once an alert is triggered, the 10 second timer opens the relay via U2 and causes a cessation of electrosurgical power for that interval and illuminates the red LED.

Figure 5A:
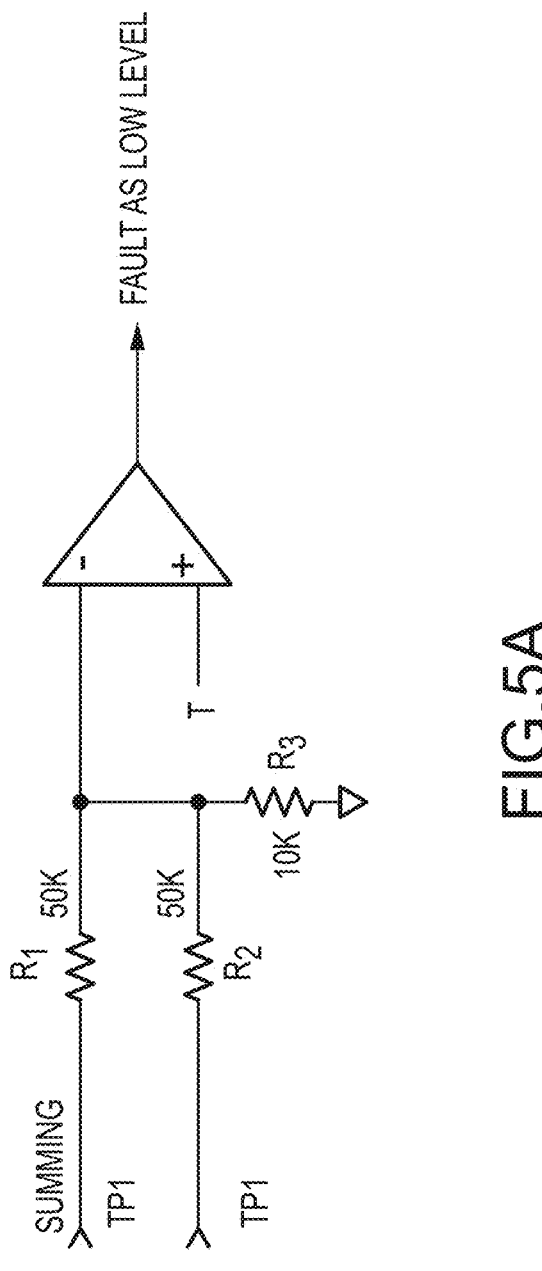
FIGS. 5A-5C are circuit diagrams of embodiments of alternative fault detectors of the present invention.
Figure 5B:
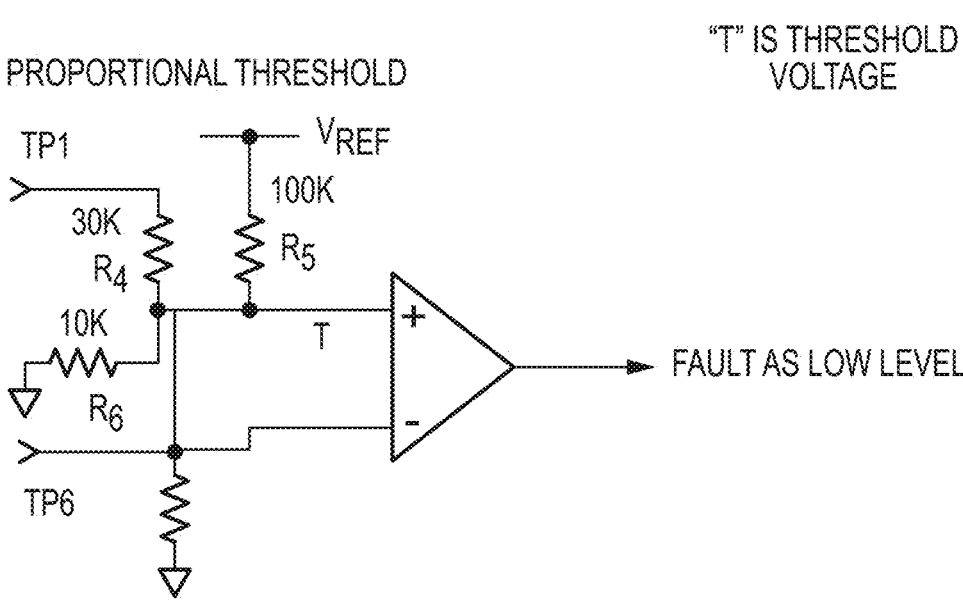
Figure 5C:
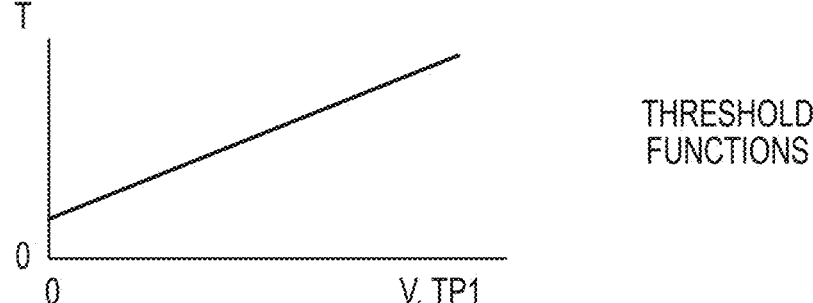

Turning now to FIGS. 5A-5C, other embodiments of a portion of the monitoring circuitry 106 are shown. As seen in FIG. 5A, a SUM function may be incorporated, such that the average shield current, which may be a wideband average current, is summed with the current peak. If the sum is greater than a present threshold value, a fault condition is indicated. For example, analog outputs of the current average and peak channels are summed prior to the comparator function, and this may be achieved by way of a resistor network. In this case, a fault signal is generated when the sum of the peak and shield current average channels is above a preset threshold value. One advantage to this arrangement is that, when the total signal begins to approach the preset threshold value, the system is inherently more sensitive to small increases in the peak channel response, which reduces the likelihood of a false negative response to a spark through insulation.

In FIGS. 5B and 5C, it is shown that a PROPORTIONAL function may be used instead. Here, a comparator for the peak sensing channel is supplied with a variable threshold value, rather than a fixed threshold value. It should be understood that, to prevent an indeterminate output state under low signal conditions, a fixed base is supplied, so that the comparator always has a non-zero reference input. The variable threshold value may be accomplished using a resistor network connected to the output of the shield current average channel. In the PROPORTIONAL function, a fault signal is generated when the output of the peak channel is greater than the variable threshold value. One advantage of using the PROPORTIONAL function is that more sensitive detection of an insulation sparking condition is made possible at low current operating level, as compared to the circuitry having the OR function of FIG. 3.

In some embodiments, the OR function may be combined with a SUM function and/or a PROPORTIONAL function, so as to provide desired increased sensitivity at lower operating levels as approaching preset threshold values.

Figure 6:
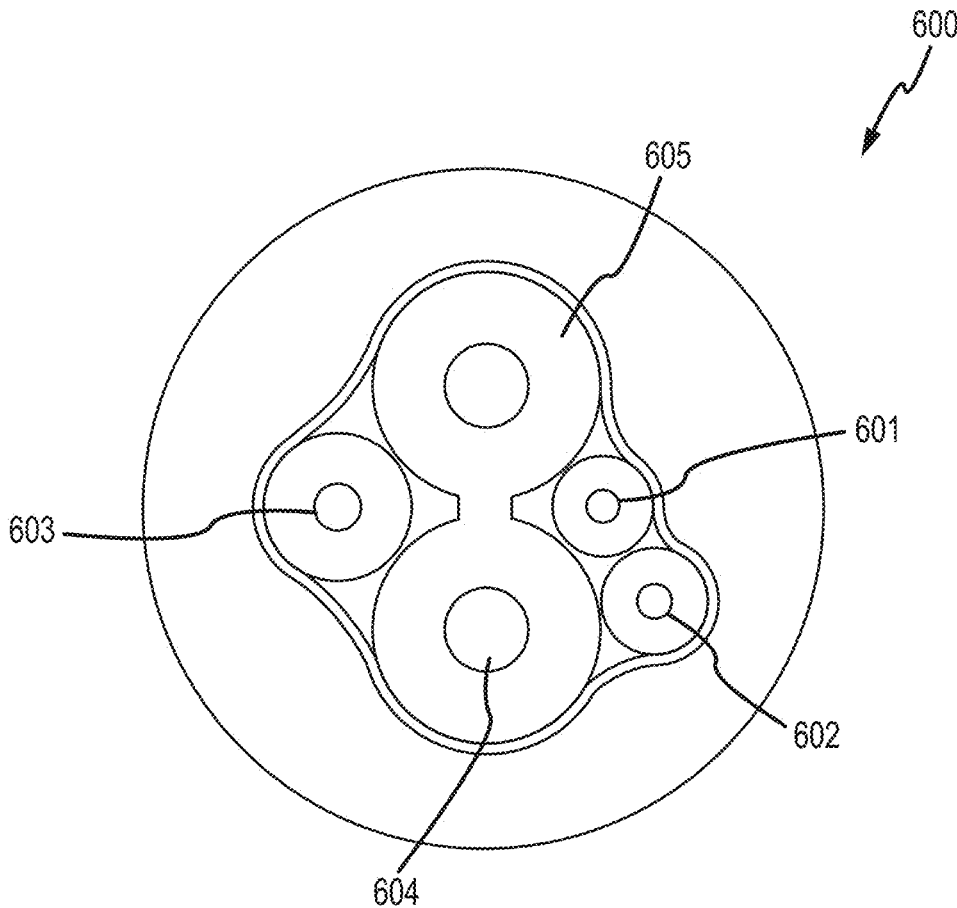
FIG. 6 is a section view of a cable according to one embodiment of the present invention.

Turning now to FIG. 6, a cable 600 for use with device 100 is now discussed. As previously mentioned, various cables or wires can be sheathed together to improve cable management, and here, cable 600 comprises shield wire 601, shield wire 602, and active wire 603. Each of the wires 601, 602, 603 is individually sheathed, and all are sheathed together in outer sheath 606. Further, string fillers 604 and pvc filler 605 and/or other low dielectric constant materials are provided to ensure adequate spacing between the wires 601, 602, 603 while maintaining low capacitance and adequate flexibility of the cable 600. The arrangement of cable 600 as shown in FIG. 6 enables high voltages to be carried through the active wire 603 without modification for use in a monopolar device; that is, prior art techniques requiring substantially reducing the voltage experienced by the active wire 603 are not required in cable 600, and thus in device 100.

Figure 7:
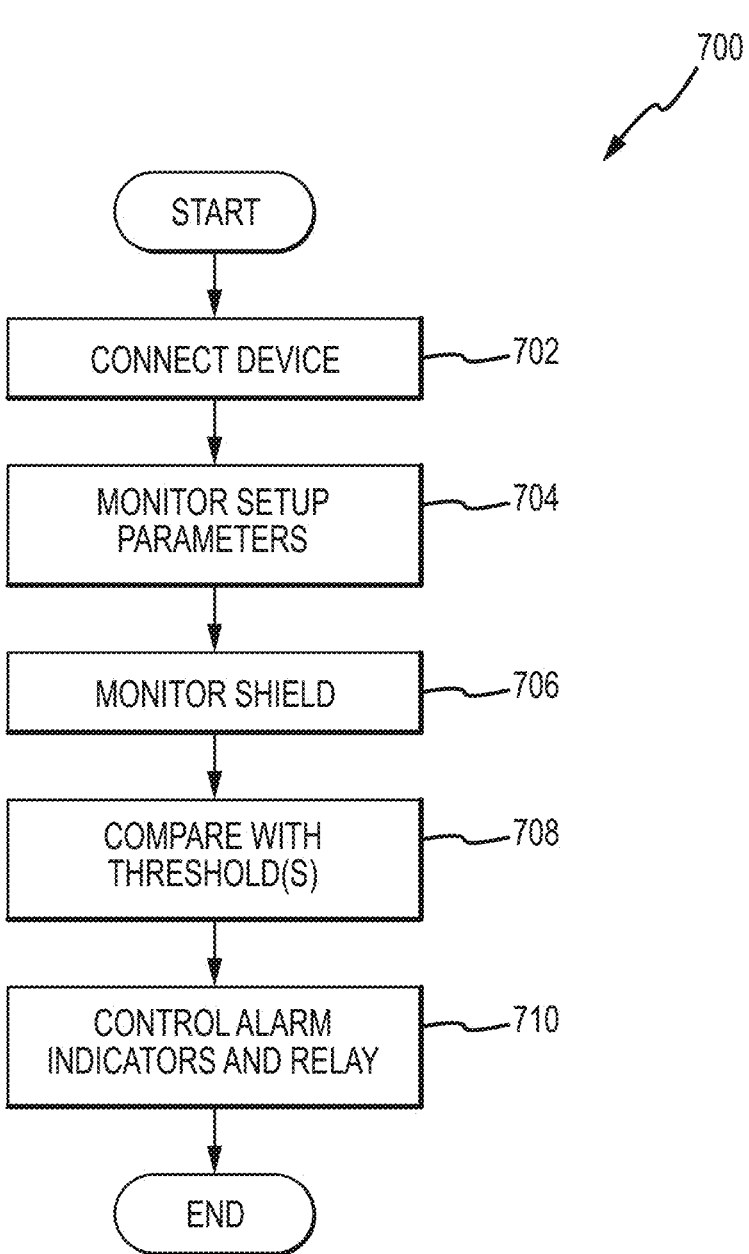
FIG. 7 is a flow chart of one embodiment of a method according to an embodiment of the present invention.

Turning now to FIG. 7, some embodiments of a method 700 are now described. The method comprises coupling a device 702 for detecting faults, monitoring setup signals 704, monitoring shield signals 706, generating dependent variables 708, comparing signals and dependent variables to threshold value(s) 710, and controlling alarm indicators 712.

Coupling the device 702 comprises coupling the device to an electrosurgical generator 4 and an electrosurgical instrument 6 that has a shield 116. One or both of the electrosurgical generator 4 and the electrosurgical instrument 6 may be similar to the electrosurgical generator 4 and electrosurgical instrument 6 discussed above with reference to FIGS. 1-5. It should be understood that the device 100 may be coupled to the electrosurgical instrument 6 before or after the device 100 is coupled to the electrosurgical generator 4. In some embodiments, coupling the device 702 to the electrosurgical generator 4 may be achieved by coupling a return electrode connector 2 to a return electrode connector 10 of the electrosurgical generator 4. The return electrode connector 2 may be configured to operatively couple both a shield current a return electrode current to the return electrode connector 10 by way of the device 100. The return electrode connector 10 may further be configured to receive a pin to actuate a pin switch 144. Coupling the device 702 to the electrosurgical generator 4 may further comprise connecting a pre-attached active cable link 3 to an active connector 5 of the electrosurgical generator 4. Coupling the device 702 to the electrosurgical instrument may be include connecting an active electrode cable 112 to the electrosurgical instrument 6. The active electrode cable 112 may be pre-attached to the device 100.

Monitoring setup signals 704 comprises monitoring a shield circuit to detect connection of a shield, as well as monitoring for low battery power of the device itself.

Monitoring shield current values 706 comprises monitoring electrical quantities associated with the shield current. The electrical quantities of the shield current may include the current peak value and the detected average current value captured and calculated respectively at a given time. The detected average current value may be a wideband average, such as, but not limited to, an FWRA value, or an RMS value, for example. The electrical quantities associated with the shield current may include the detected average, real power in the shield, the root mean square of the real part of the shield current, the RMS of the total current in the shield, the RMS of the total current in the shield below a certain active electrode voltage (referenced to the return electrode), the magnitude of the impedance or capacitance between the active electrode and the shield, the resistance between the active electrode and the shield, and the active electrode voltage (referenced to the return electrode) in combination with other quantities. A more complete understanding of monitoring shield signals 706 may be had by referencing the previous FIGS. 1-5C and the preceding discussion of device 100.

In some embodiments, monitoring shield signals 706 may comprise generating dependent variables based on the signals monitored. The dependent variables may be, for example, a SUM of the detected average current and the current peak, or a PROPORTION of the detected average current to the current peak Comparing 708 to threshold values may comprise comparing the shield current peak value to a shield current peak threshold value and comparing the detected average shield current value to a detected average shield current threshold value. Sensing a fault condition may further initiate an audible warning 134 and or a visual warning, such as a red LED 128.

In some embodiments, comparing 708 to threshold values may comprise comparing a dependent variable to a threshold dependent variable value, such as a SUM value or a PRO-PORTION value to a threshold sum value or a threshold proportion value.

Comparing 708 to threshold values may also include comparing a portion of the voltage of the independent battery power source 104 to a device voltage reference, which, in some embodiments, may be 1.24V.

The method 700 further includes controlling 710 alarm indicators and a relay. Controlling 710 comprises indicating ready conditions and closing a relay when the device is in a ready condition, as discussed previously in this document. Controlling 710 may comprise indicating fault conditions and opening a relay if a fault is detected. Controlling 710 may include alerting a user when the voltage of the battery power source 104 drops to a predetermined threshold voltage. The predetermined threshold voltage should be greater than the voltage specification of the monitoring circuitry 106 and control circuitry 108 of the device 100. In some embodiments, the threshold voltage may be about 2.6V.

The method 700 may include applying power to the electrosurgical instrument 6, determining that the shield current peak value is greater than the shield current peak threshold value, and interrupting power to the electrosurgical instrument 6. The method 700 may include determining that the detected average shield current value is greater than the detected average shield current threshold value, and interrupting power to the electrosurgical instrument 6. Power may be interrupted temporarily, for example, for a predetermined period of time, or power may be permanently interrupted, for example, where a permanent failure is detected. It should be understood that power interruption may be an OR function, wherein power is interrupted if any one of the shield current peak value, the detected average shield current value, shield connect sense, and battery voltage are outside a desired range. That is, any of the above values may indicate a fault condition. In some embodiments, a fault condition may be required to exist for a predetermined length of time greater than zero.

In an alternative embodiment, the method 700 may include applying power to the electrosurgical instrument 6, determining that a summation of the shield current peak value and the detected average shield current value is greater than a summation threshold value, and interrupting power to the electrosurgical instrument 6. Here, it should be understood that power interruption may be an OR function, wherein power is interrupted if the current summation value or the battery voltage are outside a desired range. That is, either of the above two values may indicate a fault condition. In some embodiments, a fault condition may be required to exist for a predetermined length of time greater than zero.

The method 700 may include applying power to the electrosurgical instrument 6, determining that a fault condition in the shield 116 exists, and interrupting power to the electrosurgical instrument 6 for a predetermined length of time. The predetermined length of time may be around 10 seconds, or any other length of time suitable for ensuring excess heat is dissipated from the fault site.

In conclusion, the present invention provides, among other things, a device, system and method for detecting faults in an electrosurgical instrument shield. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A fault detection device for an electrosurgical system, the fault detection device comprising:
   a shield continuity circuit configured to test electrical continuity across a shield of an electrosurgical instrument;
   a relay configured to control power to the electrosurgical instrument, the relay operable between a closed state for allowing power delivery and an open state for interrupting power;
   an indicator assembly comprising a first indicator element and a second indicator element, wherein the first indicator element is enabled when the relay is in the closed state and the second indicator element is enabled when the relay is in the open state;
   a current-to-voltage converter configured to convert a shield current to a voltage signal;
   an envelope detector configured to monitor a converted voltage signal and detect a peak shield current value;
   a shield current average detector configured to determine an average shield current value;
   a fault detection circuit configured to compare the peak shield current value and the average shield current value to one or more preset threshold values and to open the relay and illuminate the second indicator element if either of the peak shield current value or the average shield current value exceeds its respective threshold for a predetermined period of time;
   a timer configured to limit power interruption; and
   a battery-powered low battery detector configured to monitor a battery charge and illuminate the second indicator element upon detecting a low battery condition.

2. The fault detection device of claim 1, wherein the fault detection circuit further comprises an OR function, wherein a fault is detected if either the peak shield current value or the average shield current value exceeds the one or more preset threshold values.

3. The fault detection device of claim 1, wherein the fault detection circuit further comprises a SUM function, wherein a fault is detected if a sum of the peak shield current value and the average shield current value exceeds the one or more preset threshold values.

4. The fault detection device of claim 3, wherein the fault detection circuit requires the sum of the peak shield current value and the average shield current value to exceed the one or more preset threshold values for a predetermined length of time before detecting a fault.

5. The fault detection device of claim 1, wherein the fault detection circuit further comprises a PROPORTIONAL function, wherein a fault is detected if a ratio between the peak shield current value and the average shield current value deviates from the one or more preset threshold values.

6. The fault detection device of claim 5, wherein the fault detection circuit requires the ratio to deviate from the one or more preset threshold values for a predetermined length of time before detecting a fault.

7. The fault detection device of claim 1, further comprising an audible warning system configured to emit an audible warning upon fault detection for a predetermined time period.

8. The fault detection device of claim 1, wherein the relay is configured to interrupt power to the electrosurgical instrument within 130 milliseconds upon detecting a fault.

9. The fault detection device of claim 1, wherein the fault detection circuit is configured to detect electrical noise and prevent false fault detection by requiring the peak shield current value and the average shield current value to exceed the one or more preset threshold values for a predetermined period of time.

10. The fault detection device of claim 1, further comprising a cable for use with the electrosurgical instrument comprising:
   a first shield wire;
   a second shield wire;
   an active wire for carrying high voltage;
   an outer sheath encompassing the first shield wire, the second shield wire, and the active wire; and
   a plurality of fillers positioned within the outer sheath, wherein the plurality of fillers include string fillers and a low dielectric constant material configured to maintain spacing between the first shield wire, the second shield wire, and the active wire, thereby reducing capacitance and preserving a flexibility of the cable;
   wherein the active wire is configured to carry high voltage without voltage modification for use in a monopolar device.

11. A method for detecting and responding to fault conditions in an electrosurgical system, the method comprising:

monitoring electrical continuity across a shield of an electrosurgical instrument using a shield continuity circuit;

converting a shield current to a voltage signal using a current-to-voltage converter;

detecting a peak shield current value using an envelope detector;

calculating an average shield current value using a shield current average detector;

comparing the peak shield current value and the average shield current value to one or more preset threshold values;

interrupting power to the electrosurgical instrument by opening a relay if either the peak shield current value or the average shield current value exceeds its respective threshold;

illuminating an indicator element to indicate a fault condition when the relay is opened;

limiting power interruption to a predetermined time period using a timer; and emitting an audible warning for a predetermined time period upon fault detection.

12. The method of claim 11, further comprising using an OR function to detect a fault if either the peak shield current value or the average shield current value exceeds the one or more preset threshold values.

13. The method of claim 11, further comprising using a SUM function to detect a fault if a sum of the peak shield current value and the average shield current value exceeds the one or more preset threshold values.

14. The method of claim 13, wherein the sum of the peak shield current value and the average shield current value must exceed the one or more preset threshold values for a predetermined length of time before detecting a fault.

15. The method of claim 11, further comprising using a PROPORTIONAL function to detect a fault if a ratio between the peak shield current value and the average shield current value deviates from the one or more preset threshold values.

16. The method of claim 15, wherein the ratio must deviate from the one or more preset threshold values for a predetermined length of time before detecting a fault.

17. The method of claim 11, wherein power to the electrosurgical instrument is interrupted within approximately 130 milliseconds upon detecting a fault.

18. The method of claim 11, further comprising preventing false fault detection by requiring the peak shield current value and the average shield current value to exceed the one or more preset threshold values for a predetermined period of time.

19. The method of claim 11, wherein the method is powered by an independent battery source, and a low battery detector is configured to monitor a battery charge and illuminate the indicator element upon detecting a low battery condition.

20. The method of claim 11, wherein the peak shield current value further includes one or more of: a root mean square (RMS) value of a shield current, a real part of a shield current, an impedance or capacitance between an active electrode and a shield, a resistance between an active electrode and a shield, and an active electrode voltage referenced to a return electrode.

* * * * *